United States Patent [19]

George et al.

[11] 3,994,159
[45] Nov. 30, 1976

[54] HOLDING FOR TENSILE TESTING FABRICS

[75] Inventors: McLean George; Rose L. Glee, both of New Orleans, La.

[73] Assignee: The United States of America as represented by the Secretary of Agriculture, Washington, D.C.

[22] Filed: Nov. 5, 1975

[21] Appl. No.: 629,479

[52] U.S. Cl. ............................................. 73/103
[51] Int. Cl.² ......................................... G01N 3/04
[58] Field of Search ..................... 73/103, 95, 159; 24/141; 292/314; 85/50 R, 50 AT

[56] References Cited
UNITED STATES PATENTS 2,850,895  9/1958  Mereness et al. .................... 73/103
3,487,680  1/1970  Eichenbrenner et al. ............ 73/103

Primary Examiner—Jerry W. Myracle
Attorney, Agent, or Firm—M. Howard Silverstein; Salvador J. Cangemi; David G. McConnell

[57] ABSTRACT

An apparatus for holding fabric samples during tensile testing under constant temperature and wet conditions comprising a pair of clamping jaws between which is held a fabric sample, secured by a standard metal eyelet which is inserted through a hole provided in said jaws and sample for said eyelet.

3 Claims, 4 Drawing Figures

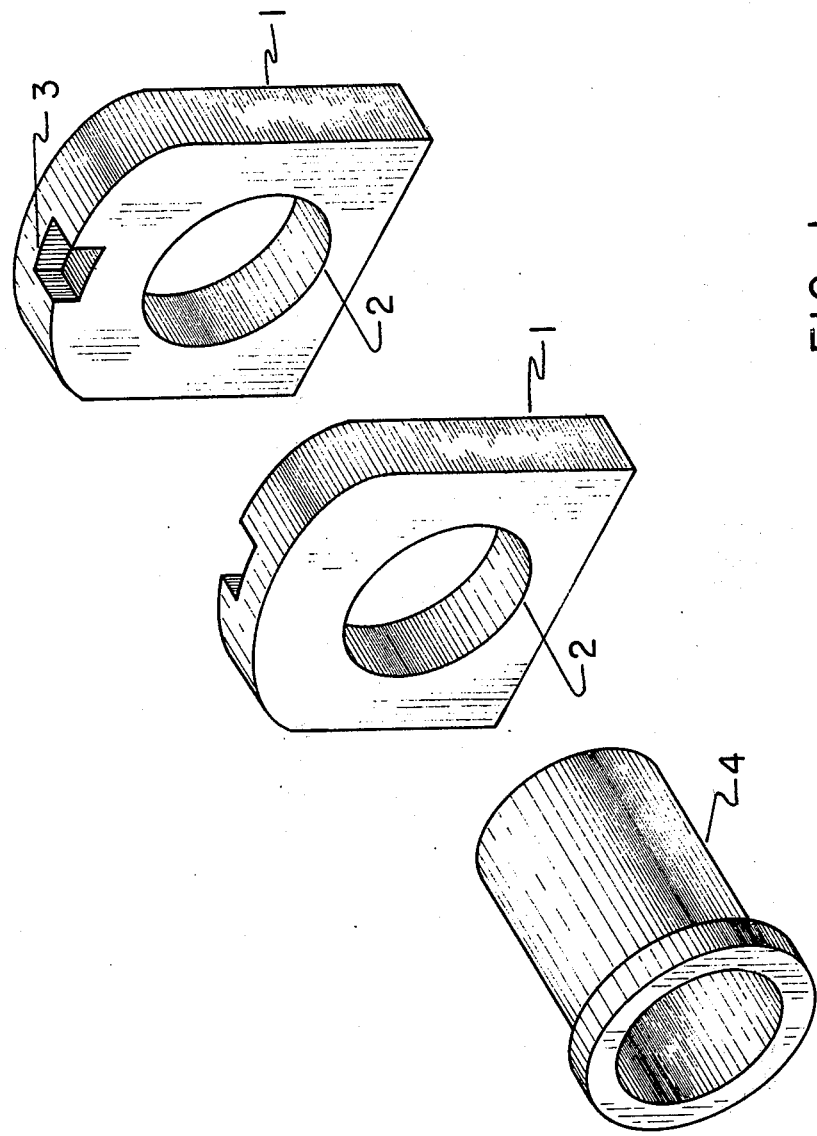

HOLDING FOR TENSILE TESTING FABRICS

An apparatus for tensile testing of fabrics under controlled temperature and wet conditions is described. Even more specifically, this apparatus consists of a new device for holding textile fabrics in tension under laboratory controlled conditions which will allow for accurate, concise, and repeatable results while constant temperature and wet conditions are maintained.

It has long been known in the art that tensile testing of fabrics could easily be accomplished. However, with the advent of testing procedures requiring controlled temperature and wet conditions, the bulky and cumbersome jaws and clamping devices for holding samples during tensile testing would not lend themselves to sufficient modification so as to be immersed into a narrow cylindrical container which was necessary for maintaining the controlled temperature and wet conditions. Therefore, it was necessary to develop a new method of continually circulating water through a glass column mounted onto an Instron Tensile Strength Tester while testing fabric specimens submerged in solution. Consequently, a unique eyelet-clamping device to hold the specimens under these restricted conditions was devised. Accurate data produced from these tests resulted in valuable conclusions as to the differences in resiliency observed between polyester-cotton broadcloth fabrics at various water temperatures.

It is the principal object of this invention to provide a means for holding fabric specimens during tensile testing. It is yet another object of this invention to hold a fabric specimen during tensile testing under constant temperature and wet conditions. A third object of this invention is to provide a holding apparatus for fabric in tension to achieve accurate repeatable data.

Other objects and advantages of this invention will further become apparent hereinafter and in the drawings, in which:

FIG. 1 is an exploded isometric view of the holding apparatus.

Figure 3:
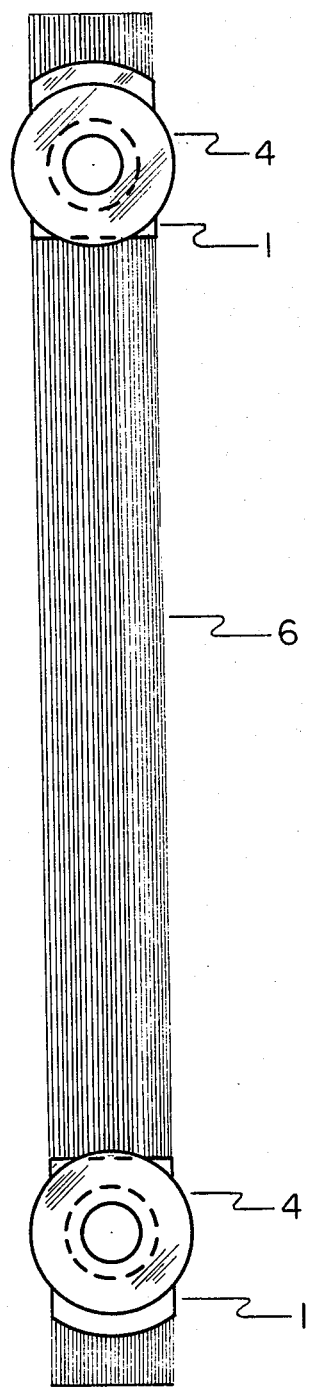
FIG. 3 is a front view showing the holding apparatus assembled to a fabric sample.

In describing the preferred embodiment of the invention illustrated in the drawings, specific terminology will be resorted to for the sake of clarity. However, it is not intended to be limited to the specific terms so selected, and it is to be understood that each specific term includes all technical equivalents which operate in a similar manner to accomplish a similar purpose.

Figure 2:
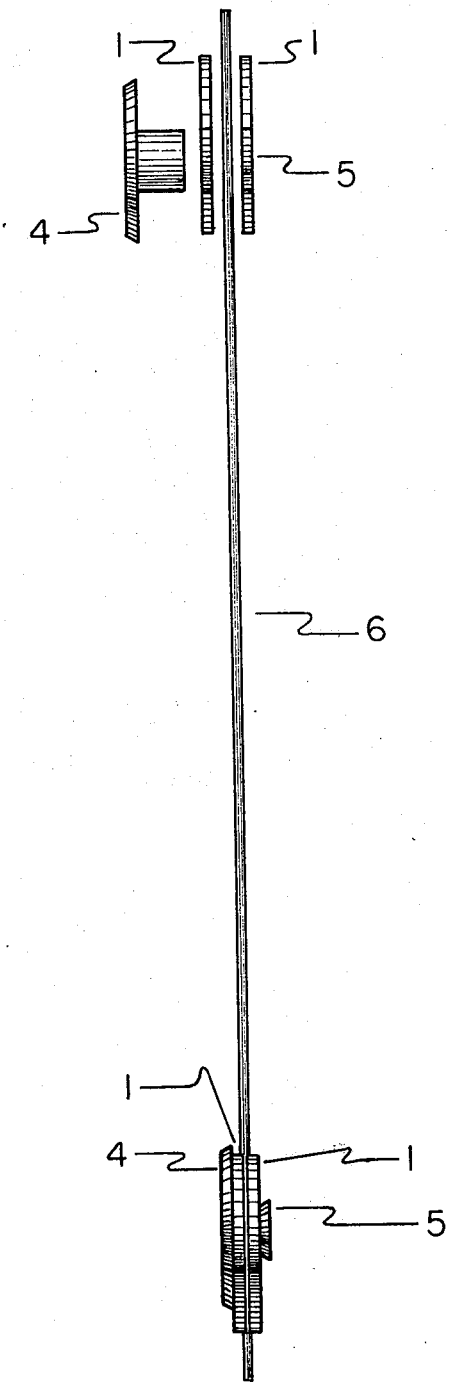
FIG. 2 is a side view showing how the jaws and eyelet of the holding apparatus is assembled to the fabric sample.
Figure 4:
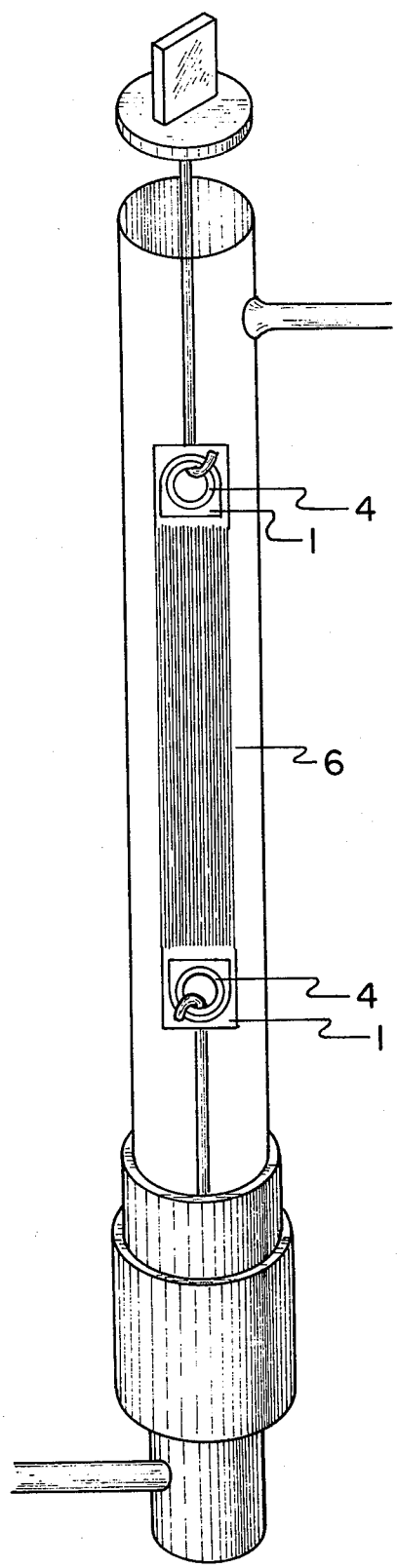
FIG. 4 shows the method in which the sample is installed in the glass cylinder for constant temperature wet sampling in tension.

Turning now to the specific embodiment of the invention illustrated in the drawings, where the number 1, FIGS. 1–4, represents one side or one-half of the jaw arrangement, the jaws 1 have a hole 2 in the center thereof and are used in pairs for clamping a sample fabric 6, FIGS. 2–4. For the instant invention, instead of the 1 × 6 inch raveled strip recommended by ASTM-D 1682 64[2] for fabric breaking load and elongation tests, a ½ × 7½ inch specimen is required. Dimensions were changed to accommodate the modified test unit shown in FIG. 4 which has an inside diameter of approximately 11/16 inches and because the standard eyelets 4 FIGS. 1–4 available cover a 9/16 inch diameter of the fabric thereby making a larger test unit or specimen impractical. However, the only criteria as to size limitation is the specimen to testing apparatus ratio. These fabrics are then raveled ⅛ inch on each side starting 1¼ inches from the ends to give a 5 inch specimen ¼ inch wide. Both ends of the fabric are then coated several times with Ubabond glue to provide stability and stiffness to the yarns at the ends to be clamped. Holes of sufficient size to allow for the passage of the eyelets 4 are punched into both ends of the specimen. The jaws 1 are positioned on each side of the fabric holes so that the holes 2 line up with the holes in the fabric. After this operation is accomplished both ends of the fabric samples and eyelet 4 is inserted through the jaws 1 and fabric 6 thus clamping the fabric in between the jaws 1 with the fabric 6 in the middle and held tightly, FIGS. 2 and 3. The eyelet 4 is then flared on the end to hold the assembly tightly for testing.

Jaws 1 are made of metal or other rigid material 1/10 inches thick, 6/10 inches long and 6/10 inches wide. These dimensions were found to be most compatible with the head of the eyelet and yet perform the testing function efficiently. It was also found that the slot 3 located in the rounded top of jaws 1 and used for removing the jaws on disassembly is most efficient when it is 3/10 inch × 1/10 inch × 1/20 inch for each half.

The eyelet 4 is a standard metal eyelet having a shaft slightly less than diameter of the hole in the flat metal plates and a round head with a diameter exceeding the outside diameter of the eyelet shaft. This allows for the eyelet to be inserted through the holes in the plates up to the eyelet head. The shaft is of sufficient length to allow for the end opposing the head end to be flared and thus a rigid holding of a fabric sample inserted between the flat metal plate jaws can be sustained. It is necessary then to have the eyelet hollow throughout the center thereof to allow for the flaring operation after the eyelet is inserted through the plate jaws.

The fabric is then assembled in the testing apparatus as shown in FIG. 4, which is a wet testing apparatus consisting of a glass column and inlet and outlet connections at the top and bottom. In actual operation, the glass column is placed into the bottom jaw base and then connected to the top crosshead of an Instron tensile tester. The fabric sample is assembled inside the glass column to top and bottom sealing members using wire hooks inserted through the eyelet holding apparatus. Water or other fluid is circulated through the glass cylinder by means of the inlet and outlet connections which are hooked up to an outside fluid source which is connected to a constant temperature fluid bath. The temperature is maintained constant by a heating means.

Once the apparatus is assembled the test may be performed by means of lowering or raising the crosshead of the Instron Tensile Tester. In the case of the instant invention, the modified immersion unit was used on the Instron Tensile Strength Tester Model TT with settings of 2 inches per minute crosshead speed and 5 inches per minute chart speed.

Once the test is complete disassembly is simple. The water is drained from the glass column and the fabric sample removed from the container. The jaws 1 can be removed from the fabric sample by use of a standard flat head screw driver. The flat end is placed in slot 3 and a prying motion will free the two jaw halves from the eyelet. Since the eyelet 4 had been flared on the end, it is usually discarded and a new eyelet used for each subsequent test.

Having thus described our invention we claim:

1. An apparatus for the holding of fabric samples during tensile testing under constant temperature and wet conditions comprising in combination:
    a. a pair of clamping jaws comprising:
        1. flat metal plates each plate rounded on one end substantially forming a top end, said top end notched to one half the thickness of the flat metal plate and of sufficient width and depth to allow for the flat end of a standard flat metal screw driver to be inserted, and
        2. said flat metal plates having a hole located through the center thereof,
    b. a standard metal eyelet, said eyelet having a diameter shaft slightly less than the diameter of the hole in the flat metal plates and a round head with a diameter exceeding the outside diameter of the eyelet shaft, said eyelet shaft and head being hollow substantially the length thereof which allows for inserting the eyelet through the metal plate jaws when assembled with a fabric cloth sample in between the said jaws, said jaws being held rigidly by the eyelet head on one side and said eyelet shaft flared on the opposing side.

2. The apparatus as defined in claim 1 wherein the flat metal plates are 1/10 inch × 6/10 inch × 6/10 inch for each half.

3. The apparatus as defined in claim 1 wherein the flat metal plates are notched at the center of the round top end said notch being 1/10 inch × 3/10 inch × 1/20 inch.

* * * * *